(12) United States Patent
Cilip et al.

(10) Patent No.: US 10,261,028 B2
(45) Date of Patent: Apr. 16, 2019

(54) DEVICE FOR OPTICALLY INSPECTING A SURFACE OF A SAMPLE

(71) Applicant: Carl Zeiss Industrial Metrology, LLC, Maple Grove, MN (US)

(72) Inventors: Christopher M. Cilip, Maple Grove, MN (US); Drew Schiltz, Champlin, MN (US)

(73) Assignee: Carl Zeiss Industrial Metrology, LLC, Maple Grove, MN (US)

( * ) Notice: Subject to any disclaimer, the term of this patent is extended or adjusted under 35 U.S.C. 154(b) by 73 days.

(21) Appl. No.: 15/430,046

(22) Filed: Feb. 10, 2017

(65) Prior Publication Data

US 2017/0227471 A1 Aug. 10, 2017

Related U.S. Application Data

(60) Provisional application No. 62/293,581, filed on Feb. 10, 2016.

(51) Int. Cl.
*G01N 21/88* (2006.01)
*H04N 7/18* (2006.01)

(52) U.S. Cl.
CPC ......... *G01N 21/8851* (2013.01); *H04N 7/183* (2013.01)

(58) Field of Classification Search
CPC .......................... H04N 7/183; G01N 21/8851
See application file for complete search history.

(56) References Cited

U.S. PATENT DOCUMENTS

| 5,726,705 A * | 3/1998 | Imanishi | G01N 21/8806 348/92 |
| 5,745,236 A * | 4/1998 | Haga | G01N 21/8806 356/237.1 |
| 6,815,702 B2 * | 11/2004 | Kiermeier | B41F 27/005 101/477 |
| 2005/0111726 A1 * | 5/2005 | Hackney | G01B 11/2513 382/145 |
| 2007/0147821 A1 * | 6/2007 | Gaessler | G01N 21/55 396/155 |
| 2015/0070499 A1 * | 3/2015 | Roelke | G03B 15/00 348/148 |

FOREIGN PATENT DOCUMENTS

EP 2167947 B1 * 12/2007
WO 2009007130 A1 1/2009

* cited by examiner

*Primary Examiner* — Tsion B Owens
(74) *Attorney, Agent, or Firm* — Walter Ottesen, P.A.

(57) ABSTRACT

A device for optically inspecting a surface of a sample includes: a screen providing a first light profile pattern formed with lighter and darker areas wherein the areas form a first spatial intensity profile having a first spatial period, a holder for positioning the sample with the surface relative to the first pattern such that the first pattern is reflected by the surface, an auxiliary lens and/or curved mirror arranged between the screen and the holder for providing a second light profile pattern having areas which form a second spatial intensity profile with a second spatial period when at least a part of the first pattern passes the lens or is reflected by the mirror, an image recording unit for receiving an image of the second pattern reflected from the surface of the sample, and an evaluation unit for determining properties of the surface in dependence on the image.

18 Claims, 2 Drawing Sheets

DEVICE FOR OPTICALLY INSPECTING A SURFACE OF A SAMPLE

CROSS REFERENCE TO RELATED APPLICATION

This application claims priority of U.S. provisional patent application No. 62/293,581, filed Feb. 10, 2016, the entire content of which is incorporated herein by reference.

FIELD OF THE INVENTION

The present invention relates to a device for optically inspecting a surface of a sample.

BACKGROUND OF THE INVENTION

In the industrial production of products product quality plays an increasingly important role. High quality can be achieved on the one hand by appropriately configured, stable production processes. On the other hand, the quality parameters of a product must as exactly as possible be controlled reliably and completely to recognize quality defects at an early stage. In many cases the quality of a surface plays an important role for the product properties. The products may be decorative surfaces such as painting surfaces in motor vehicles, or technical surfaces such as the surface of finely machined metal pistons or bearings.

There are a variety of proposals and concepts to automatically examine such surfaces. Deflectometry is for at least partially reflective surfaces a very promising concept, in which a pattern of lighter and darker areas will be considered over the surface to be inspected. The pattern is shifted relative to the surface. Due to the changes which the inspected areas undergo by the reflection, it is possible to inspect the reflective surface visually. For example, the local slope of a surface point is determined of at least three images with different relative positions of the pattern. With the local inclinations then scratches, pores, bumps, cavities and other dimensional defects can be detected. Also gloss level and scattering properties of the surface can be determined by the deflectometry.

WO 2009/007130 A1 discloses a device wherein the surface is inspected using the deflectometry. All details on the deflectometric evaluation, which are disclosed in WO 2009/007130 A1, are intended to be incorporated herein by reference. The known device includes a tunnel having an inner wall which is provided with a pattern. An article having the surface to be inspected, in this case a motor vehicle, is moved through the tunnel. Meanwhile the surface to be inspected is recorded with multiple cameras. Due to the relative movement of the surface to the pattern the pattern "migrates" from the perspective of the cameras across the surface. For the practical realization of the method, it is advantageous if each surface point to be inspected is recorded at at least four different positions relative to the pattern, wherein the at least four different positions cover exactly one period of the intensity profile. In the process according to WO 2009/007130 A1 this may be achieved in that the moving speed of the motor vehicle is adjusted accurately in the tunnel to the geometric conditions of the pattern in the tunnel.

SUMMARY OF THE INVENTION

Against this background, it is an object of the present invention to provide an alternative device to inspect a surface in a largely automated, fast, and reliable manner and with high accuracy. The device should be universally applicable and should be implemented cost-effectively.

This object is, for example, achieved by a device for optically inspecting a surface of a sample, wherein the device includes:

a screen providing a first light profile pattern formed with a multiplicity of lighter and darker areas wherein the areas form a first spatial intensity profile having a first spatial period, a holder for the sample for positioning the sample with the surface relative to the first light profile pattern such that the first light profile pattern is becoming reflected by the surface, an auxiliary lens and/or an auxiliary curved mirror arranged between the screen and the holder for providing a second light profile pattern having areas which form a second spatial intensity profile with a second spatial period when at least a part of the first light profile pattern is passed through the auxiliary lens or is reflected by the auxiliary mirror, an image recording unit for receiving an image of the second light profile pattern being reflected from the surface of the sample, and an evaluation unit for determining properties of the surface in dependence on the image.

According to an embodiment of the invention the screen is provided on an inside wall of a tube member.

According to a further embodiment of the invention the auxiliary lens or the auxiliary curved mirror is cylindrical having a cylindrical axis of symmetry.

According to a further embodiment of the invention the image recording unit includes a single line camera.

According to a further embodiment of the invention the image recording unit includes a single line camera which is arranged parallel to the cylindrical axis of symmetry.

According to a further embodiment of the invention the evaluation unit is configured to generate a phase image based on a plurality of images recorded by the image recording unit.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
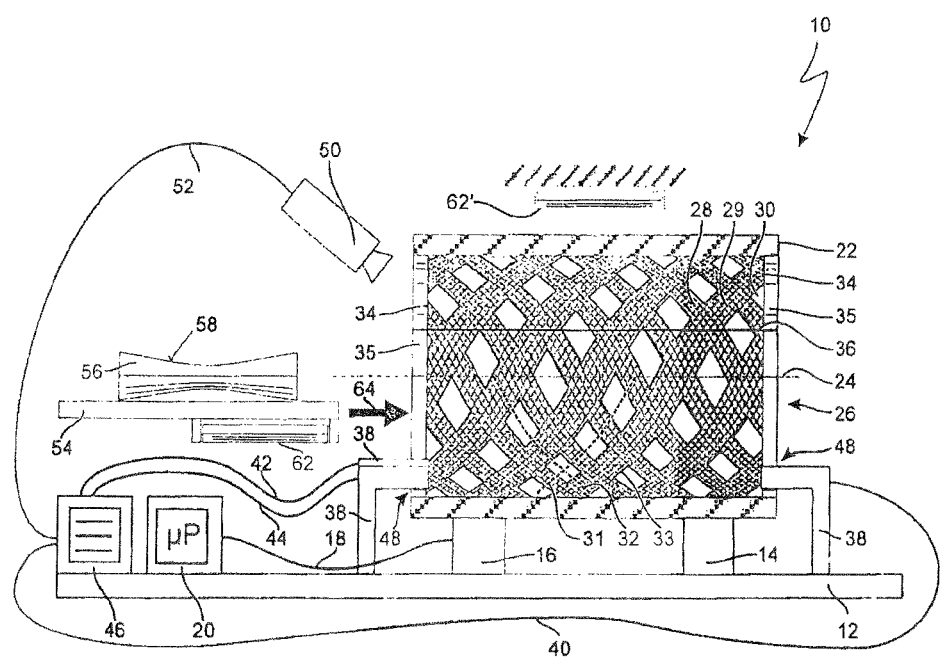
FIG. 1 is a simplified and schematic representation of a first embodiment of the device for optically inspecting a surface of a sample with a measuring unit in a side view, wherein the sample is located outside of the device.

FIG. 1 shows a partial sectional side view of a measurement device 10 according to a first embodiment of the invention. The device 10 includes a base plate 12 which is disposed on holding elements 14, 16. The holding element 16 includes a drive and is connected via a line 18 with a control unit 20.

The holding elements 14, 16 support a tube member 22 which has a longitudinal axis 24. In an embodiment the tube member 22 is made of a light translucent material. The longitudinal axis 24 is oriented parallel to the base plate 12.

Thus, the holding elements 14, 16 support the tube member 22 at its outer tube surface in a manner that the tube member 22 can be rotated about its longitudinal axis 24.

A foil 26 is attached to the inside surface of the tube member 22. The foil 26 serves as a carrier element for a pattern 28. The pattern 28 includes darker areas 29 and lighter areas 30. A darker area 29 together with a consecutive lighter area 30 define two crossing periodic intensity profiles 31, 32 each having a spatial period and a defined period length. In an embodiment the darker and lighter areas form a pattern with rectangular intensity profiles 31, 32. In this embodiment the intensities at a particular point 33 jump from a low value directly and unsteadily to a high value and otherwise from a high value to a low value. In another embodiment the intensity profiles or profiles can be sinusoidal, or in different manners continuous and steady. The intensity profiles show in FIG. 1 results from two superimposed groups of linear fringe patterns which are oriented perpendicular to one another, wherein the fringe period in each group is constant but different between both groups. Perpendicular to the extension of the group of fringe patterns the first intensity profile 31 and the second intensity profile 32 of the pattern result. The groups of fringe patterns can have different fringe periods.

The pattern 28 terminates at edges 34 which extend along the circumference of the inner casing of the tube member 22. At each one of the edges 34 a respective marking area 35 can be provided. In an embodiment only a single marking area 35 can be provided.

For clarity reasons, the marking areas 35 are shown in FIG. 1 without showing details of the marks. The marking areas 35 are applied on the foil 26 together with the pattern 28 to ensure that the marking areas 35 are in a fixed geometrical relationship to the pattern 28. The marking areas 35 cooperate with optical sensors 38, wherein one marking area 35 on the left side of the device according to FIG. 1 cooperates with two optical sensors 38 and another marking area 35 on the right side of the device according to FIG. 1 cooperates with a single optical sensor 38.

The optical sensors 38 are connected to an evaluation unit 46 via lines 40, 42, 44. The evaluation unit 46 evaluates the information provided by the sensors 38 and, based on this, determines the actual position of the intensity profiles 31, 32. The optical sensors 38 together with the marking areas 35 form a measuring unit 48 which allows to determine the actual positions of the intensity profiles 31, 32.

For optically inspecting a surface 58 of a sample 56 an image recording unit 50, for example a camera, is provided and arranged so that it can gather an image of the interior room of the tube member 22. Also the image recording unit 50 is connected to the evaluation unit 46 via a line 52. The evaluation unit 46 evaluates the images recorded by camera 50 for inspecting the surface 58 of the sample 56 and for determining properties of the sample 56.

The device 10 further includes a carrier element 54 for sample 56 with the surface 58 which is to be inspected. In FIG. 1 the sample 56 is shown mounted on the carrier element 54. Below the carrier element 54 a first light source 62 is provided, which provides sufficient illumination during the optical inspection. In addition, above the tube member 22 an alternative or additional second light source 62' can be provided. The second light source 62' also provides a sufficient illumination of the interior room of the tube member 22 during inspection process if the material of the tube member 22 is light translucent. The carrier element 54 can be moved to move the sample 56 into the interior room of the tube member 22.

A control unit 20 controls the drive of the holding element 16 in a manner that the tube rotates about its longitudinal axis 24. For providing a sufficient illumination of the surface 58 of the sample 56 the first light source 62 is switched on so that it generates a cone of light 70. Alternatively or additionally, the second light source 62' can be switched on for providing a sufficient illumination of the interior room of the tube member 22 during inspection process.

For inspecting the surface 58 of the sample 56 a series of images of the surface 58 of the sample 56 is recorded by the image recording unit 50, whereby the tube member 22 is rotated between successive recordings of images. As a result of this rotation of the tube member 22 the intensity profiles 31, 32 are positioned differently in different recorded images relative to the surface 58 of the sample 56. Advantageously, for each point on the surface 58 to be inspected at least four images are recorded, wherein each point on the surface 58 to be measured has a different position relative to the intensity profiles 31, 32. In addition it is advantageous if the four images cover exactly one full fringe period of the intensity profiles. In the latter case the four images can be analyzed very easily according to the so called "Four-Bucket-Method" in optical deflectometry as this, for example, is described in WO 2009/007130 A1. For this the images recorded by the recording unit 50 are transmitted to the evaluation unit 46.

Figure 2:
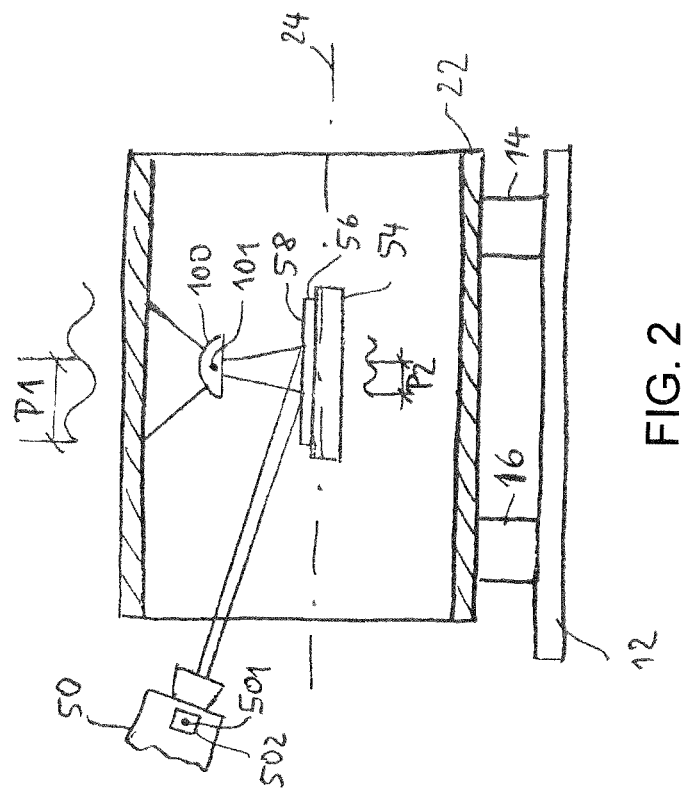
FIG. 2 is a schematic representation of the device according to FIG. 1 in a side view wherein the sample is located inside of the device; and, FIG. 3 is a schematic representation of the device according to FIG. 2 in a partial sectional top view.

The inspection of the surface 58 of the sample 56 is carried out within a recording region 72, see FIG. 2, which includes the surface 58 to be inspected. A surface which is too large to become completely inspected within the recording region 72 can become inspected by repeated inspection of the sample with a shifting of the sample along the extension of the longitudinal axis 24 between successive inspections.

The rotational movement of the tube member 22 is detected by the measurement unit 48 and also transmitted to the evaluation unit 46. By means of the measurement signals provided by the measurement unit 48 the evaluation unit 46 determines the degree of rotation of the pattern (and accordingly the intensity profiles) relatively to the surface 58 of the sample between successive image recordings. In addition it can be determined whether regions of the pattern, for example the edges 36, have been registered by the recording unit 50. In an embodiment, the evaluation unit 46 controls the rotational movement of the tube member 22 via the signals provided by the measurement unit 48 which are a measurement of the actual rotational position of the tube member 22 and along the control unit 20. In addition, in particular embodiments the evaluation unit 46 triggers the recording of the images by the recording unit 50 in dependence on the actual rotational position of the tube member 22 (and accordingly in dependence on the actual position of the intensity profiles 31, 32) in a manner that the point in time of the image recording is defined by the actual rotational position of the tube member 22.

Based on the images recorded by image recording unit 50 by different positions of the pattern relative to the surface 58 of the sample 56 and forming different linear combinations of the intensity values recorded for the same point on the sample surface in the different images. At least three different image types can be generated. The first image type is a synthetically generated grey-scale image, which shows the brightness profile of the images of the surface 58 of the sample 56 in the case of a homogenous illumination of the surface 58. The second image type is a modulation image which shows the contrast profile of the images of the surface 58 of the sample 56 in the case of a homogenous illumination. The third image type is a phase image which shows the phase profile of the recorded patterns. The phase image shows for each point on the surface 58 of the sample 56 within the inspected region the surface topography modulo $2\pi$. Within the modulation image a changing glare of the surface 58 of the sample 56 can be recognized very easily. Especially shiny regions can be differentiated very easily from dim regions within the modulation image.

The three image types of the inspected surface 58 of sample 56—synthetic grey-scale image, modulation image and phase image—generated based on the originally recorded images with different phase positions between the surface of the sample and the pattern form a set of measurement values generated by the described device which can be used for further evaluation and qualification of the sample 56. For particular inspection tasks it can be desirable to provide a light profile pattern with a different periodicity on the surface of the sample than the pattern provided on the inside surface or screen of the tube member 22. If this is the case an auxiliary lens 100 or a curved mirror can be arranged in the interior room of the tube member 22 between the wall or screen of the tube member 22 and the holder 54 of the sample 56 to be inspected, preferably between the screen and the surface 58 of the sample 56, as shown in FIG. 2. The lens 100 can be a collecting lens having a positive refractive power or a collecting mirror. In the case where the screen displays a first light profile pattern formed with a multiplicity of lighter and darker areas wherein the areas form a first spatial intensity profile having a first spatial period P1, then this first light profile pattern can pass through the auxiliary lens 100 so that behind the auxiliary lens 100 a second light profile pattern is formed having areas which form a second spatial intensity profile with a second spatial period P2. Alternatively, the lens 100 can be substituted by a collecting mirror which transfers a first light profile pattern into a second light profile pattern by means of reflection.

The lens 100 can be used to increase the frequency of the fringe pattern on the surface 58 of the sample 56. Due to the increased frequency of the pattern the height resolution of the inspection system based on the phase image will become increased so that smaller topographical changes can become resolved without changing the field of view of the images recorded by image recoding unit 50.

Alternatively, for particular inspection tasks it can become desirable to decrease the frequency of the fringe pattern. In this case a defocusing lens having a negative refractive power or a convex mirror can be arranged in the interior room of tube member 22 between the screen of the tube member 22 and the surface 58 of the sample 56 to be measured. A reduced fringe or pattern frequency can be desirable if samples with very steep topographical changes of very rough and strongly scattering surfaces are to be inspected.

In addition it is possible to provide a combination of a lens and a curved mirror arranged in the interior room of tube member 22 between the walls or the screen of the tube and the surface 58 of the sample 56 to be measured to reduce optical aberrations which would be caused by a single lens or a single mirror alone.

The lens 100 can be a cylindrical lens or a cylindrical mirror having a light collecting effect only in a single direction which is perpendicular to the direction of the cylindrical lens or mirror. For example in FIG. 2, lens 100 can have a cylindrical axis 101 oriented perpendicular to the drawing plane. The resulting pattern which will become effective for inspecting the surface 58 of sample 56 then has a changed or increased pattern frequency in the direction parallel to the extension of the cylindrical axis 101, that is, in the drawing plane of FIG. 2, but an unchanged pattern frequency perpendicular to the extension of the cylindrical axis 101. This arrangement can be desirable if only in one direction an increased sensitivity for topographical changes is necessary because, for example, only irregularities with a very small dimension in one direction and a considerable longer dimension in the perpendicular direction, such as scratches, are to be identified. If respective features such as scratches in different directions are to be identified two consecutive measurements with different orientations of the sample relative to the direction of the cylinder lens can be performed.

Figure 3:
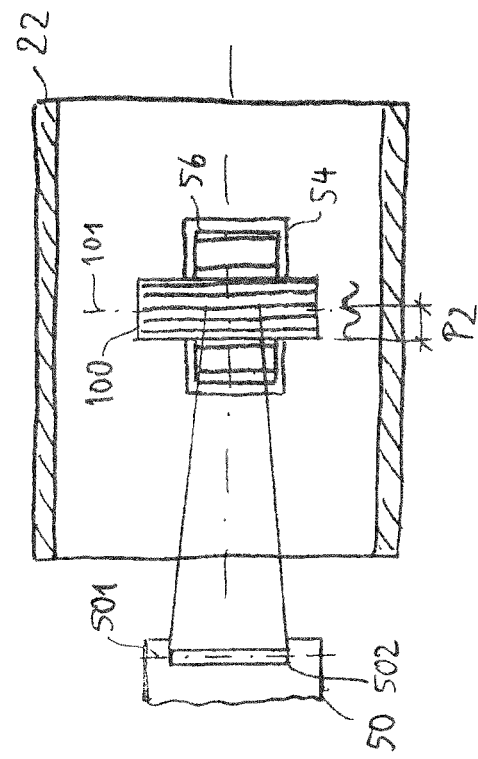

In the embodiment according to FIGS. 2 and 3 the image recording unit 50 can be a single line camera such as a single line CCD camera having a series of light sensitive elements arranged along a single line wherein the elements form a line sensor 502 having a sensor axis 501. In this case the images recorded by the image recording unit 50 are line images consisting of measured light intensities along a single line.

In a combination with the cylindrical lens 100 or mirror arranged in the interior room of the tube member 22 between the wall or screen of the tube member 22 and the surface 58 of sample 56 to be measured the orientation of the single line camera can be arranged such that the sensor axis 501 is arranged parallel to the extension of the cylindrical axis 101.

It is understood that the foregoing description is that of the preferred embodiments of the invention and that various changes and modifications may be made thereto without departing from the spirit and scope of the invention as defined in the appended claims.

What is claimed is:

1. A device for optically inspecting a surface of a sample, wherein the device comprises:
   a screen configured to provide a first light profile pattern formed with a multiplicity of lighter and darker first areas wherein said lighter and darker first areas form a first spatial intensity profile having a first spatial period;
   a holder for the sample configured for positioning the sample with the surface relative to said first light profile pattern such that said first light profile pattern is reflected by the surface;
   an auxiliary lens and an auxiliary curved mirror arranged between said screen and said holder and configured to provide a second light profile pattern having second areas which form a second spatial intensity profile with a second spatial period when at least a part of said first light profile pattern is passed through said auxiliary lens or is reflected by said auxiliary mirror;
   an image recording unit configured to receive an image of said second light profile pattern being reflected from the surface of the sample; and,
   an evaluation unit configured to determine properties of the surface in dependence on said image.

2. The device of claim 1, further comprising:
   a tube member having an inner wall; and,
   said screen being provided on said inner wall of said tube member.

3. The device of claim 1, wherein said auxiliary lens or said auxiliary curved mirror is cylindrical and defines a cylindrical axis of symmetry.

4. The device of claim 1, wherein said image recording unit includes a single line camera.

5. The device of claim 3, wherein said image recording unit includes a single line camera which is arranged parallel to said cylindrical axis of symmetry.

6. The device of claim 1, wherein said evaluation unit is configured to generate a phase image based on a plurality of images recorded by said image recording unit.

7. A device for optically inspecting a surface of a sample, wherein the device comprises:
   a screen configured to provide a first light profile pattern formed with a multiplicity of lighter and darker first areas wherein said lighter and darker first areas form a first spatial intensity profile having a first spatial period;
   a holder for the sample configured for positioning the sample with the surface relative to said first light profile pattern such that said first light profile pattern is reflected by the surface;
   an auxiliary lens arranged between said screen and said holder and configured to provide a second light profile pattern having second areas which form a second spatial intensity profile with a second spatial period when at least a part of said first light profile pattern is passed through said auxiliary lens;
   an image recording unit configured to receive an image of said second light profile pattern being reflected from the surface of the sample; and,
   an evaluation unit configured to determine properties of the surface in dependence on said image.

8. The device of claim 7, further comprising:
   a tube member having an inner wall; and,
   said screen being provided on said inner wall of said tube member.

9. The device of claim 7, wherein said auxiliary lens is cylindrical and defines a cylindrical axis of symmetry.

10. The device of claim 7, wherein said image recording unit includes a single line camera.

11. The device of claim 9, wherein said image recording unit includes a single line camera which is arranged parallel to said cylindrical axis of symmetry.

12. The device of claim 7, wherein said evaluation unit is configured to generate a phase image based on a plurality of images recorded by said image recording unit.

13. A device for optically inspecting a surface of a sample, wherein the device comprises:
   a screen configured to provide a first light profile pattern formed with a multiplicity of lighter and darker first areas wherein said lighter and darker first areas form a first spatial intensity profile having a first spatial period;
   a holder for the sample configured for positioning the sample with the surface relative to said first light profile pattern such that said first light profile pattern is reflected by the surface;
   an auxiliary curved mirror arranged between said screen and said holder and configured to provide a second light profile pattern having second areas which form a second spatial intensity profile with a second spatial period when at least a part of said first light profile pattern is reflected by said auxiliary mirror;
   an image recording unit configured to receive an image of said second light profile pattern being reflected from the surface of the sample; and,
   an evaluation unit configured to determine properties of the surface in dependence on said image.

14. The device of claim 13, further comprising:
   a tube member having an inner wall; and,
   said screen being provided on said inner wall of said tube member.

15. The device of claim 13, wherein said auxiliary curved mirror is cylindrical and defines a cylindrical axis of symmetry.

16. The device of claim 13, wherein said image recording unit includes a single line camera.

17. The device of claim 15, wherein said image recording unit includes a single line camera which is arranged parallel to said cylindrical axis of symmetry.

18. The device of claim 13, wherein said evaluation unit is configured to generate a phase image based on a plurality of images recorded by said image recording unit.

* * * * *